(12) United States Patent
Alhadeff et al.

(10) Patent No.: US 11,123,351 B2
(45) Date of Patent: *Sep. 21, 2021

(54) PHARMACEUTICAL FORMULATION OF 3-ALPHA-ETHYNYL-3-BETA-HYDROXYANDROSTAN-17-ONE OXIME

(71) Applicant: Umecrine Cognition AB, Solna (SE)

(72) Inventors: Paul Alhadeff, Uttran (SE); Magnus Doverskog, Stockholm (SE); Maja Johansson, Vannas (SE); Thomas Meijer, Segeltorp (SE); Nicolaas Schipper, Ronninge (SE)

(73) Assignee: Umecrine Cognition AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/797,426

(22) Filed: Feb. 21, 2020

(65) Prior Publication Data
US 2020/0297737 A1   Sep. 24, 2020

Related U.S. Application Data

(63) Continuation of application No. 16/450,620, filed on Jun. 24, 2019, now Pat. No. 10,603,326, which is a continuation of application No. PCT/EP2018/082727, filed on Nov. 27, 2018.

(60) Provisional application No. 62/590,757, filed on Nov. 27, 2017.

(51) Int. Cl.
| | |
|---|---|
| *A61K 31/568* | (2006.01) |
| *A61P 1/16* | (2006.01) |
| *A61K 9/48* | (2006.01) |
| *A61K 47/14* | (2017.01) |
| *A61K 31/7016* | (2006.01) |
| *A61K 31/437* | (2006.01) |

(52) U.S. Cl.
CPC ............. *A61K 31/568* (2013.01); *A61K 9/48* (2013.01); *A61K 47/14* (2013.01); *A61P 1/16* (2018.01); *A61K 31/437* (2013.01); *A61K 31/7016* (2013.01)

(58) Field of Classification Search
None
See application file for complete search history.

(56) References Cited

U.S. PATENT DOCUMENTS

| | | |
|---|---|---|
| 6,994,862 B2 | 2/2006 | Jeong et al. |
| 2004/0191207 A1 | 9/2004 | Lipari et al. |
| 2010/0209496 A1 | 8/2010 | Dokou et al. |
| 2012/0244215 A1 | 9/2012 | Giliyar et al. |
| 2013/0029957 A1 | 1/2013 | Giliyar et al. |
| 2014/0271832 A1 | 9/2014 | Lee |
| 2017/0348323 A1 | 12/2017 | Backstrom et al. |
| 2019/0358244 A1 | 11/2019 | Alhadeff et al. |

FOREIGN PATENT DOCUMENTS

| | | |
|---|---|---|
| WO | WO-1995/24893 A1 | 9/1995 |
| WO | WO-1997/40823 A1 | 11/1997 |
| WO | WO-1998/30206 A1 | 7/1998 |
| WO | WO-2000/59482 A1 | 10/2000 |
| WO | WO-2008/063128 A1 | 5/2008 |
| WO | WO-2011/087441 A1 | 7/2011 |
| WO | WO-2015/114308 A1 | 8/2015 |
| WO | WO-2015/193224 A1 | 12/2015 |
| WO | WO-2016/033556 A1 | 3/2016 |
| WO | WO-2017/116190 A1 | 7/2017 |
| WO | WO-2017/196148 A1 | 11/2017 |

OTHER PUBLICATIONS

Constantinides, Lipid microemulsions for improving drug dissolution and oral absorption: physical and biopharmaceutical aspects. Pharm Res. Nov. 1995;12(11):1561-72.
Cremer Care, Inspired by nature, IMWITOR® 742, INCI: Caprylic/Capric Glycerides. Cremer Oleo GmbH & Co. KG, 3 pages, Mar. 2013.
Crews et al., Quantitation of the main constituents of some authentic sesame seed oils of different origin. J Agric Food Chem. Aug. 23, 2006;54(17):6266-70.
Gupta et al., Formulation strategies to improve the bioavailability of poorly absorbed drugs with special emphasis on self-emulsifying systems. ISRN Pharm. Dec. 26, 2013;2013:848043, 16 pages.
Hauss, Oral lipid-based formulations. Adv Drug Deliv Rev. Jul. 30, 2007;59(7):667-76.
Johansson et al., GR3027 Antagonizes the Effect of an Allopregnanolone-challenge in Humans. 9th International Meeting Steroids and Nervous System. pp. 161-162, Feb. 11-15, 2017.
Johansson et al., GR3027 reverses neurosteroid-induced, GABAA receptor-mediated inhibition of brain function: a human challenge study. Journal of Hepatology. 2017;66:S387, Abstract FRI-046.
Kalepu et al., Oral lipid-based drug delivery systems—an overview. Acta Pharmaceutica Sinica B. Dec. 2013;3(6):361-372.
Kalepu et al., Insoluble drug delivery strategies: review of recent advances and business prospects. Acta Pharmaceutica Sinica B. Sep. 2015;5(5):442-453.
Lindenberg et al., Classification of orally administered drugs on the World Health Organization Model list of Essential Medicines according to the biopharmaceutics classification system. Eur J Pharm Biopharm. Sep. 2004;58(2):265-78.
Nanjwade et al., Functions of lipids for enhancement of oral bioavailability of poorly water-soluble drugs. Sci Pharm. Oct.-Dec. 2011;79(4):705-27.

(Continued)

*Primary Examiner* — Brian J Davis
(74) *Attorney, Agent, or Firm* — McCarter & English, LLP; Steven G. Davis; Mei Bai

(57) ABSTRACT

The present invention is directed to a novel pharmaceutical formulation comprising 3α-ethynyl-3β-hydroxyandrostan-17-one oxime in an amount of 0.1-10% by weight of the total weight of the composition; and a vehicle comprising (a) 45-100% of a monoester; (b) optionally up to 51% of a diester; and (c) optionally up to about 10% of a triester. Also claimed is a method for the treatment of medical conditions such as hypersomnia and hepatic encephalopathy by the use of a pharmaceutical formulation as claimed.

22 Claims, 3 Drawing Sheets

(56) References Cited

OTHER PUBLICATIONS

Parul et al.. Bioavailability Enhancement of Poorly Soluble Drugs by SMEDDS: A Review. Journal of Drug Delivery & Therapeutics. 2013;3(1):98-109.

Patil et al., Effect of formulation variables on preparation and evaluation of gelled self-emulsifying drug delivery system (SEDDS) of ketoprofen. AAPS PharmSciTech. Jul. 22, 2004;5(3):e42, 8 pages.

Pouton, Self-emulsifying drug delivery systems: assessment of the efficiency of emulsification. International Journal of Pharmaceutics. Dec. 1985;27(2-3):335-348.

Schwarz et al., Solubilizing steroidal drugs by beta-cyclodextrin derivatives. Int J Pharm. Oct. 15, 2017;531(2):559-567.

Umecrine cognition, Umecrine Cognition announces first patient included in clinical Phase 2a study in patients with sleep disorder. 1 page, Nov. 20, 2017.

Umecrine cognition, Umecrine Cognition announces positive top-line Phase 1 data with GR3027 in hepatic encephalopathy demonstrating safety, tolerability and CNS target engagement. 2 pages, Nov. 3, 2016.

Umecrine cognition, Umecrine Cognition announces first patient included in clinica Phase 1b/2a study with GR3027, a novel drug candidate for Hepatic Encephalopathy. 2 pages, Mar. 17, 2017.

Umecrine cognition, Umecrine Cognition announces positive data from its phase 1b study of GR3027—a potential new treatment of hepatic encephalopathy. 2 pages, Sep. 13, 2017.

Plasma concentration of IND compound (mean ± SEM) after a singel oral dose (six subjects per dose).

Plasma concentration of the IND compound (mean ± SEM) after a singel oral dose (MAD first dose).

Plasma concentration of the IND compound (mean ± SEM) after repeated dosing for five days (MAD last dose).

PHARMACEUTICAL FORMULATION OF 3-ALPHA-ETHYNYL-3-BETA-HYDROXYANDROSTAN-17-ONE OXIME

CROSS-REFERENCE TO RELATED APPLICATIONS

This application is a continuation of U.S. patent application Ser. No. 16/450,620, filed on Jun. 24, 2019, which is a continuation of International Application No. PCT/EP2018/082727, filed Nov. 27, 2018, which claims priority to U.S. Provisional Application No. 62/590,757, filed Nov. 27, 2017. The entire teachings of each of the aforementioned applications are incorporated herein by reference.

FIELD OF THE INVENTION

The present invention is directed to a novel pharmaceutical formulation, uses thereof in therapy such as in the treatment of medical conditions such as hypersomnia and hepatic encephalopathy.

BACKGROUND OF THE INVENTION

One of the largest challenges in pharmaceutical drug development is that drug compounds very often are insoluble, or poorly soluble, in aqueous media. Insufficient drug solubility in turn means insufficient bioavailability and poor plasma exposure of the drug when administered to subjects such as humans and animals.

It is estimated that between 40% and 70% of all new chemical entities identified in drug discovery programs are insufficiently soluble in aqueous media (M. Lindenberg, S et al.: *European Journal of Pharmaceutics and Biopharmaceuticals*, vol. 58, no. 2, pp. 265-278, 2004; D. J. Hauss: *Drugs and Pharmaceutical Sciences*, Vol. 170, pp. 1-339, Informa Healthcare NC, 2007).

Gupta et al.; Volume 2013, Article ID 848043 Review Article http://dx.doi.org/10.1155/2013/848043

Scientists have investigated various ways of solving the problem with low drug solubility in order to enhance bioavailability of poorly absorbed drugs, aiming at increasing their clinical efficacy when administered orally. Technologies such as increase of the surface area and hence dissolution may sometimes solve solubility problems. Other techniques that may also solve bioavailability problems are addition of surfactants and polymers. However, each chemical compound has its own unique chemical and physical properties, and hence have its own different challenges when being formulated into a pharmaceutical drug that can exert its clinical efficacy.

Formulating a drug in different types of lipids are useful for particular drugs. Lipid formulations for oral administration generally consist of a drug dissolved in a blend of excipients with a wide variety of physicochemical properties ranging from pure triglyceride oils, mono- and diglycerides, and a substantial portion of lipophilic or hydrophilic surfactants and co-solvents.

The main considerations in selecting appropriate excipients for any lipid-based formulation is identifying one or more excipients which have the ability to solubilise the complete dose and which at the same time provides a formulated unit dosage of the drug that can be taken orally and being of a size that can be swallowed by the patient. Usually, the drug load in combination with the size of a tablet or capsule is a limiting factor.

Lipid-based formulations may contain one lipid only, or a mixture of different types of lipids in combination. It is also common that in formulating a poorly soluble drug, it is required to also include one or more additional excipients to obtain a satisfactory solubility as well as drug stability. Pharmaceutical formulations comprising several types of lipid systems in combinations often tend to be complicated to produce and hence the cost of goods increases.

Self-Emulsifying Drug Delivery Systems (SEDDS) may be useful to formulate poorly soluble drugs. However, very few lipid based formulations have reached the pharmaceutical market place. The edible oils which represent the logical and preferred lipid excipient choice for the development of SEDDS, are not frequently selected due to their poor ability to dissolve large amounts of lipophilic drugs. The self-emulsifiyng properties also require the incorporation of relatively large amounts of surfactant in the formulation in addition to the oily drug carrier vehicle.

A mixture of mono- and diglycerides of caprylic/capric acid (Akoline) is an emulsifyer of natural origin that is preferred since it is considered as more safe than synthetic commercially available surfactants. However, it is recognized among scientists in the pharmaceutical field that such excipients have limited self-emulsification efficiency (P. P. Constantinides; *Pharmaceutical Research*, vol. 12, no. 11. Pp. 1561-1572, 1995).

Usually, the surfactant concentration ranges between 30 and 60% of the total formulation in order to form SEDDS (C. W. Pouton; *International Journal of Pharmaceutics*, vol. 27, no. 2-3, pp. 335-348, 1985). Large amounts of surfactants may cause GI irritations. The surfactants involved in the formulation of SEDDS should have a relatively high HLB and hydrophilicity to enable rapid and facile dispersion in the aqueous GI fluid as a very fine oil-in-water emulsion, and hence good self-emulsifying performance can be achieved. Also, one or more co-solvents are often added to the formulation to assist in solubilising high concentrations of the drug.

The compound 3α-ethynyl-3β-hydroxyandrostan-17-one oxime is a compound currently in clinical Phase II for the treatment of Hepatic Encephalopathy (HE) and Hypersomnia (HS). One of the problems with this compound is that it has a poor solubility in aqueous media, and hence there is a need to find a way to formulate this compound in order to obtain a clinically and commercially feasible drug product.

DESCRIPTION OF THE INVENTION

The compound 3α-ethynyl-3β-hydroxyandrostan-17-one oxime (Compound I)

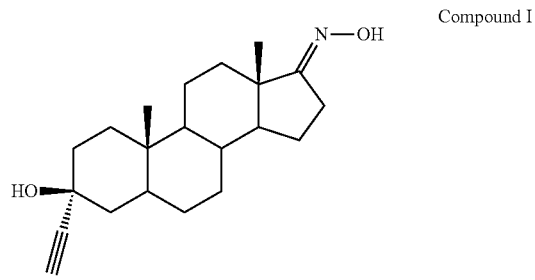 [SMILES: C#C[C@]1(O)CC[C@@]2(C)C(CCC3C2CC[C@]2(C)/C(=N/O)CCC32)C1]

Compound I has a poor solubility in aqueous media, which in turn means that the drug load is low and it is therefore difficult to reach a clinically therapeutic dose without giving patients an excessive number of drug doses. In order to make it possible to formulate this compound into a pharmaceutical drug product providing a sufficient drug load, and hence enabling the drug product to exert a clinically sufficient therapeutic effect, a new pharmaceutical formulation has been developed.

One aspect of the present invention is a pharmaceutical formulation comprising:
(i) 3α-ethynyl-3β-hydroxyandrostan-17-one oxime

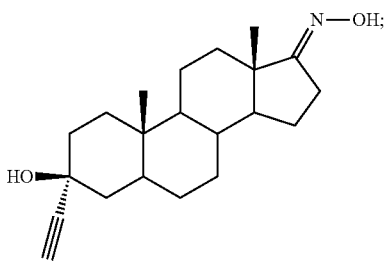 [SMILES: C#C[C@]1(O)CC[C@@]2(C)C(CCC3C2CC[C@]2(C)/C(=N/O)CCC32)C1]

and
(ii) a vehicle comprising
  a) 45-100% of a monoester;
  b) optionally up to 51% of a diester;
  c) optionally up to about 10% of a triester;
wherein the monoester, diester (if any) and/or triester (if any) comprise(s) a fatty acid selected from one or more of
  caprylic acid (C8) in an amount of 50-90%;
  capric acid (C10) in an amount of 10-50%;
  caproic acid (C6) in an amount of up to 3%;
  lauric acid (C12) in an amount of up to 100%;
  palmitic acid (C16) in an amount of up to 12%;
  myristic acid (C14) in an amount of up to 3%;
  stearic acid (C18) in an amount of up to 6%;
  oleic acid (C18:1) in an amount of up to 100%;
  linoleic acid (C18:2) in an amount of up to 35%; and
wherein
the amount of the compound 3α-ethynyl-3β-hydroxyandrostan-17-one oxime is from 0.1-10% by weight of the total weight of the composition.

In one aspect of the invention, the pharmaceutical formulation of the present invention comprises 3α-ethynyl-3β-hydroxyandrostan-17-one oxime in an amount from 0.1-10% by weight of the total weight of the composition and a vehicle comprising
(a) 45-100% of a monoester;
(b) optionally up to 51% of a diester;
(c) optionally up to about 10% of a triester;
wherein the fatty acid(s) forming the monoester(s) and the fatty acid(s) forming the optional di- and/or triester(s) is/are selected from one or more of caprylic acid (C8), capric acid (C10), caproic acid (C6), lauric acid (C12), palmitic acid (C16), myristic acid (C14), stearic acid (C18), oleic acid (C18:1), and linoleic acid (C18:2).

In one aspect, the total amount of the above fatty acid ester(s) forming the vehicle amounts to 100% of the vehicle, and the vehicle completely consists of one or more of the above fatty acid ester(s).

In one aspect of the invention, the vehicle is a monoester.
In yet an aspect of the invention, the vehicle is a mixture of a monoester and a diester.
In yet an aspect of the invention, the vehicle is a mixture of a monoester and a triester.
In yet an aspect of the invention, the vehicle is a mixture of a monoester, a diester and a triester.

The present invention is completely unexpected in that the bioavailability and drug exposure of 3α-ethynyl-3β-hydroxyandrostan-17-one oxime may be increased by formulating said compound according to the present invention.

One aspect of the invention is a pharmaceutical formulation as herein described and claimed, wherein the incorporation of surfactant or any other excipient in the formulation in addition to the vehicle is not required.

One aspect of the invention is a pharmaceutical formulation as herein described and claimed, consisting of 3α-ethynyl-3β-hydroxyandrostan-17-one oxime and the above defined vehicle only.

One aspect of the invention is a pharmaceutical formulation as herein described and claimed, consisting of 3α-ethynyl-3β-hydroxyandrostan-17-one oxime and the above defined vehicle only, wherein the above fatty acid ester(s) forming the vehicle amounts to 100% of the vehicle.

One aspect of the invention is a pharmaceutical formulation as herein described and claimed, wherein the amount of 3α-ethynyl-3β-hydroxyandrostan-17-one oxime is from 0.1-5% by weight of the total weight of the formulation.

One aspect of the invention is a pharmaceutical formulation as herein described and claimed, wherein the amount of 3α-ethynyl-3β-hydroxyandrostan-17-one oxime is from 0.1-4% by weight of the total weight of the formulation.

One aspect of the invention is a pharmaceutical formulation as herein described and claimed, wherein the amount of vehicle in said pharmaceutical formulation is from 90-99.9% by weight of the total weight of the formulation.

One aspect of the invention is a pharmaceutical formulation as herein described and claimed, wherein the amount of vehicle in said pharmaceutical formulation is 95-99.9% by weight of the total weight of the formulation.

One aspect of the invention is a pharmaceutical formulation as herein described and claimed, providing a solubility of 3α-ethynyl-3β-hydroxyandrostan-17-one oxime in the vehicle of up to 50 mg/ml.

An aspect of the invention is a pharmaceutical formulation as herein described and claimed, providing a solubility of 3α-ethynyl-3β-hydroxyandrostan-17-one oxime in the vehicle of up to 40 mg/ml.

An aspect of the invention is a pharmaceutical formulation as herein described and claimed, providing a solubility of 3α-ethynyl-3β-hydroxyandrostan-17-one oxime in the vehicle of up to 60 mg/ml.

Yet an aspect of the invention is a pharmaceutical formulation as herein described and claimed, providing a solubility of 3α-ethynyl-3β-hydroxyandrostan-17-one oxime in the vehicle of up to 100 mg/ml, such as up to 90 mg/ml, or up to 80 mg/ml, or up to 70 mg/ml, or up to 60 mg/ml, or up to 50 mg/ml, or up to 40 mg/ml, or up to 30 mg/ml, or up to 20 mg/ml, or up to 10 mg/ml.

An aspect of the invention is a pharmaceutical formulation as herein described and claimed, wherein the monoester, diester (if any) and/or triester (if any) comprises the fatty acid caprylic acid (C8) in an amount of 50-90%; and the fatty acid capric acid (C10) in an amount of 10-50%.

Examples of monoesters which may be useful in a vehicle according to the invention are monoglycerides selected from any one of glycerol monocaproate, glycerol monocaprylate, glycerol monodecanoate, glycerol monolaurate, glycerol monomyristate, glycerol monopalmitate, glycerol monostearate, glycerol monooleate, and glycerol monolinoleate.

One aspect of the invention is a pharmaceutical formulation as herein described and claimed comprising the glycerol monoesters of caprylic acid and capric acid as vehicle.

Yet further examples of monoesters which may be useful in a vehicle according to the invention are monoesters of propylene glycol selected from any one of propylene glycol caprylate, propylene glycol caproate, and propylene glycol decanoate.

Further examples of monoesters which may be useful in a vehicle according to the invention are selected from any one of propylene glycol palmitate, propylene glycol stearate, and propylene glycol linoleate.

Further examples of monoesters which may be useful in a vehicle according to the invention are esters of propylene glycol and fatty acids selected from any one of propylene glycol isostearate, propylene glycol laurate, propylene glycol myristate, propylene glycol oleate, and propylene glycol oleate SE.

Examples of diesters that may be useful in a vehicle according to the invention are di-esters of propylene glycol and fatty acids, such as any one selected from propylene glycol dicaproate, propylene glycol dicaprylate, propylene glycol didecanoate, propylene glycol dilaurate, propylene glycol dimyristate, propylene glycol dipalmitate, propylene glycol distearate, propylene glycol dioleate, and propylene glycol dilinoleate.

Still further examples of diesters that may be useful in a vehicle according to the invention are esters of glycerol and fatty acids such as any one selected from glycerol dicaproate, glycerol dicaprylate, glycerol didecanoate, glycerol dilaurate, glycerol dimyristate, glycerol dipalmitate, glycerol distearate, glycerol dioleate, and glycerol dilinoleate.

An aspect of the invention is a pharmaceutical formulation as herein described and claimed, wherein the monoester is a monoglyceride, the diester if present is a diglyceride, and the triester if present is a triglyceride.

An aspect of the invention is a pharmaceutical formulation as herein described and claimed, wherein the vehicle is a mixture of glycerol monocaprylate and glycerol monodecanoate, i.e. a mixture of the glycerol monoesters of caprylic ester and capric ester, such as e.g. Imwitor742®.

An aspect of the invention is a pharmaceutical formulation as herein described and claimed, wherein the vehicle is a mixture of mono- and diglycerides of caprylic and capric acid, such as e.g. Akoline MCM®.

An aspect of the invention is a pharmaceutical formulation as herein described and claimed, wherein the vehicle is a mixture of mono- and diglycerides of caprylic and capric acid, such as e.g. Capmul® MCM.

An aspect of the invention is a pharmaceutical formulation as herein described and claimed, wherein the vehicle is glyceryl monooleate, such as e.g. Cithrol GMO®.

An aspect of the invention is a pharmaceutical formulation as herein described and claimed, wherein the vehicle is propylene glycol monolaurate, such as e.g. Lauroglycol FCC®.

An aspect of the invention is a pharmaceutical formulation as herein described and claimed, wherein the vehicle is an oleoyl macrogol-6 glyceride, such as e.g. Labrafil M1944 CS®.

An aspect of the invention is a pharmaceutical formulation as herein described and claimed, wherein the vehicle is a polyoxyethylene-8 caprylic/capric glyceride, such as e.g. Acconon MC8-2®.

An aspect of the invention is a pharmaceutical formulation according as herein described and claimed, wherein the vehicle is propylene glycol monocaprylate, such as e.g. capryol 90® or capryol PGMC®.

An aspect of the invention is a pharmaceutical formulation as herein described and claimed, comprising a monoester, diester (if any) and/or triester (if any), of the fatty acid caprylic acid (C8) and the fatty acid capric acid (C10), wherein the amount of caprylic acid (C8) ester is 50-90% and the amount of capric acid (C10) ester is 10-50% in the vehicle of the pharmaceutical formulation of the invention.

An aspect of the invention is a pharmaceutical formulation as herein described and claimed, wherein the vehicle is caprylic acid (C8) ester in an amount of 50-90%; and capric acid (C10) ester in an amount of 10-50%, wherein the caprylic acid (C8) ester and the capric acid (C10) ester amount to a total of 100%.

FIGURES

DEFINITIONS

Figure 1:
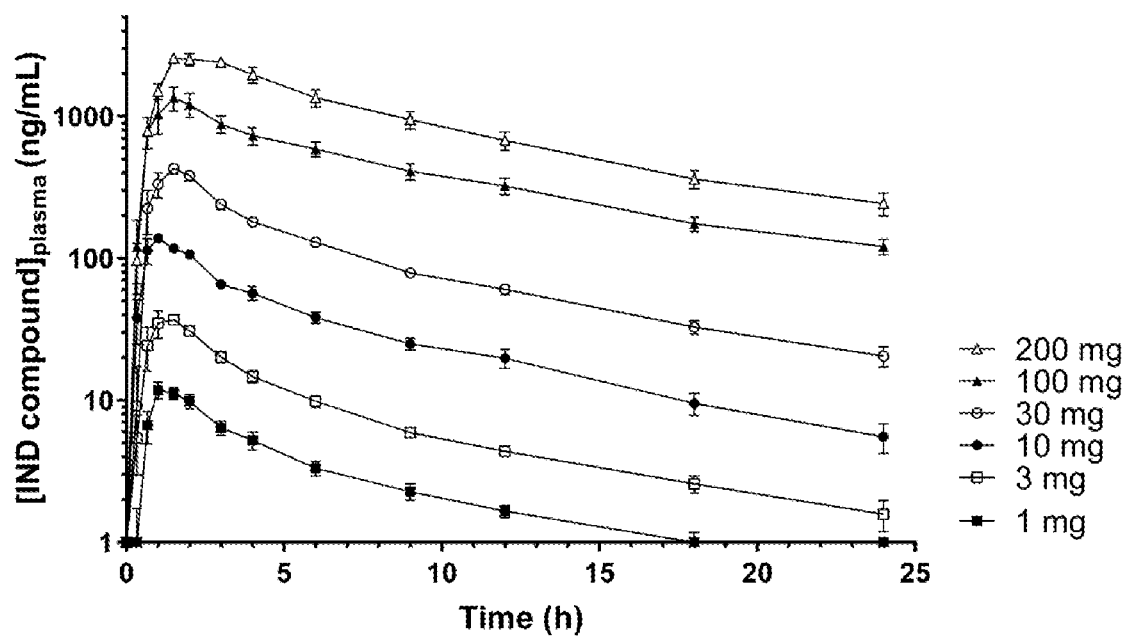
FIG. 1 is a graph showing that the plasma concentration of the IND compound 3α-ethynyl-3β-hydroxyandrostan-17-one oxime increased proportionally to the increase in dose with proportionality constants β of 1.01 for $C_{Max}$ and of 1.12 for AUC0-∞ (mean±SEM), after a single oral dose (1, 3, 10, 30, 100 and 200 mg respectively) and for six subjects per dose in the SAD study.

The wording "poorly soluble" as used herein when discussing the solubility in aqueous media of 3α-ethynyl-3β-hydroxyandrostan-17-one oxime, refers to a solubility in the µg/ml magnitude. The solubility of 3α-ethynyl-3β-hydroxyandrostan-17-one oxime has shown to be as low as 1.5 µg/ml in water, 0.2 µg/ml in SGF (Simulated Gastric Fluid), 7 µg/ml in FaSSIF (Fasted State Simulated Intestinal) and 19 µg/ml in FeSSIF (Fed State Simulated Intestinal Fluid).

The wording "IND compound" is herein defined as 3α-ethynyl-3β-hydroxyandrostan-17-one oxime (also referred to as Compound I in this patent specification).

The wording "bioequivalent product" or "product showing bioequivalence" is herein defined as a product which comprises 3α-ethynyl-3β-hydroxyandrostan-17-one oxime as therapeutic agent, in the same oral dosage form and the same dosage amount, or concentration, of said compound, and which has an identical AUC±20% and/or an identical Cmax±20%, and which shows the same or similar therapeutic effect.

The wording "Cmax" is herein defined as the maximum concentration of the therapeutic compound 3α-ethynyl-3β-hydroxyandrostan-17-one oxime which is reached at a specific time point from the time of administering the compound to a human subject.

The wording "AUC" (Area Under the Curve) is herein defined as a measure of drug absorption. A larger AUC means that the drug has a higher drug absorption in a subject, whereas a smaller AUC means that the drug has a lower drug absorption.

The wording "high amount of vehicle" as used throughout the specification, means 90-99.9% by weight of the total weight of the formulation, such as 95-99.9% by weight of the total weight of the formulation.

The wording "IND formulation" as used throughout the specification, means a pharmaceutical formulation comprising 3α-ethynyl-3β-hydroxyandrostan-17-one oxime, and used in the Clinical Phase I study described in this specification.

The wording "PK" as used throughout the specification, means pharmacokinetic properties for a compound being investigated.

The wording "SAD" is defined as "Single Ascending Dose", i.e. starting at a lower dose and increasing each dose of 3α-ethynyl-3β-hydroxyandrostan-17-one oxime in accordance with clinical trial protocol.

The wording "MAD" is defined as "Multiple Ascending Dose", i.e. starting at a lower dose and increasing each dose of 3α-ethynyl-3β-hydroxyandrostan-17-one oxime in accordance with clinical trial protocol.

The wording "once daily" as used herein, means that 3α-ethynyl-3β-hydroxyandrostan-17-one oxime, is administered to a subject only once each day.

The wording "twice daily" or "BID" as used herein, means that 3α-ethynyl-3β-hydroxyandrostan-17-one oxime, is administered in a specified dose twice each day; i.e the dose 50 mg twice daily (BID) means that the daily dose is 100 mg/day, and the wording 100 mg twice daily (BID) means that the daily dose is 200 mg/day.

The wording "vehicle" as used herein, is defined as a monoester optionally in combination with a diester and optionally also in combination with a triester.

The wording "fatty acid ester(s)" as used herein, is defined as an ester that is formed by reacting a fatty acid or a carboxylic acid with an alcohol, providing a monoester, a diester, or a triester, or a combination thereof. When the alcohol is glycerol, the fatty acid ester(s) produced may be a monoglyceride, a diglyceride, or a triglyceride, or a combination of said mono-, di-, or triglyceride.

As used herein, the percentages of fatty acids means that the total amount of a particular fatty acid or the total amount of two or more particular fatty acids should always amount to 100%. If only one fatty acid is present in forming an ester, that fatty acid content shall amount to 100% of the total amount of fatty acids; when two or more fatty acids are used, e.g. where a particular fatty acid is used for which the percentages as herein described and claimed are less than 100%, the total amount of fatty acids shall amount to a total of 100%, and so on.

The singular forms "a", "an", and "the" as used throughout this specification also include plural referents unless the context clearly states otherwise.

The wording "Type A hepatic encephalopathy" is typically meant hepatic encephalopathy associated with acute liver failure, typically associated with cerebral oedema.

The wording "Type B hepatic encephalopathy" is typically meant hepatic encephalopathy (bypass) caused by portal-system is shunting without associated intrinsic liver disease.

The wording "Type C hepatic encephalopathy" is typically meant hepatic encephalopathy occurring in patients with cirrhosis—this type is subdivided in episodic, persistent and minimal encephalopathy.

The wording "minimal hepatic encephalopathy" is typically meant hepatic encephalopathy that does not lead to clinically overt cognitive dysfunction, but can be demonstrated with neuropsychological studies.

The wording "overt hepatic encephalopathy" is typically meant clinically apparent hepatic encephalopathy manifested as neuropsychiatric syndrome with a large spectrum of mental and motor disorders. Overt hepatic encephalopathy may arise episodically, over a period of hours or days in patients previously stable or patients may present with persistent neuropsychiatric abnormalities.

The wording "hypersomnolence" may be understood to indicate a group of disorders characterised by excessive daytime sleepiness, which occurs despite the subject generally experiencing a normal quality and timing of nocturnal sleep.

The wording "narcolepsy" includes both type 1 narcolepsy (with cataplexy) and type 2 narcolepsy (without cataplexy).

Pharmaceutical Formulations and Dosing

An aspect of the invention is a pharmaceutical formulation as herein described and claimed, wherein the dose of 3α-ethynyl-3β-hydroxyandrostan-17-one oxime is from 1 mg to 200 mg.

An aspect of the invention is a pharmaceutical formulation as herein described and claimed, wherein the dose of 3α-ethynyl-3β-hydroxyandrostan-17-one oxime is from 10 mg to 100 mg.

An aspect of the invention is a pharmaceutical formulation as herein described and claimed, wherein the dose of 3α-ethynyl-3β-hydroxyandrostan-17-one oxime is from 3 mg to 30 mg.

An aspect of the invention is a pharmaceutical formulation as herein described and claimed, wherein the dose of 3α-ethynyl-3β-hydroxyandrostan-17-one oxime is from 30 mg to 60 mg.

An aspect of the invention is a pharmaceutical formulation as herein described and claimed, wherein the daily dosage of 3α-ethynyl-3β-hydroxyandrostan-17-one oxime is from 1 mg/day to 200 mg/day.

An aspect of the invention is a pharmaceutical formulation as herein described and claimed, wherein the daily dosage of 3α-ethynyl-3β-hydroxyandrostan-17-one oxime is from 50 mg/day to 100 mg/day.

An aspect of the invention is a pharmaceutical formulation as herein described and claimed, wherein the daily dosage of 3α-ethynyl-3β-hydroxyandrostan-17-one oxime is from 20 mg/day to 160 mg/day.

An aspect of the invention is a pharmaceutical formulation as herein described and claimed, wherein the daily dosage of 3α-ethynyl-3β-hydroxyandrostan-17-one oxime is from 40 mg/day to 160 mg/day.

An aspect of the invention is a pharmaceutical formulation as herein described and claimed, wherein the daily dosage of 3α-ethynyl-3β-hydroxyandrostan-17-one oxime is from 80 mg/day to 160 mg/day.

An aspect of the invention is a pharmaceutical formulation as herein described and claimed, wherein said daily dosage is administered once daily.

An aspect of the invention is a pharmaceutical formulation as herein described and claimed, wherein said daily dosage is administered twice daily.

An aspect of the invention is a pharmaceutical formulation as herein described and claimed, wherein said formulation is filled into a capsule.

An aspect of the invention is a pharmaceutical formulation as herein described and claimed, said capsule comprising from 5 mg-40 mg of 3α-ethynyl-3β-hydroxyandrostan-17-one oxime.

An aspect of the invention is a pharmaceutical formulation as herein described and claimed, said capsule comprising from 10 mg-20 mg of 3α-ethynyl-3β-hydroxyandrostan-17-one oxime.

An aspect of the invention is a pharmaceutical formulation as herein described and claimed, comprising a further therapeutic agent used as standard of care therapy for hepatic encephalopathy.

An aspect of the invention is a pharmaceutical formulation as herein described and claimed, wherein the further therapeutic agent is an ammonia-lowering compound.

An aspect of the invention is a pharmaceutical formulation as herein described and claimed, wherein the ammonia-lowering compound is selected from rifaximin, lactulose, ornithine phenylacetate, and glycerol phenylbutyrate.

An aspect of the invention is a pharmaceutical formulation as herein described and claimed, wherein the ammonia-lowering compound is rifaxamin.

An aspect of the invention is a pharmaceutical formulation as herein described and claimed, wherein the ammonia-lowering compound is lactulose.

Yet an aspect of the invention is a combination product comprising,
 (i) a pharmaceutical formulation as herein described and claimed; and
 (ii) an ammonia-lowering compound.

In yet an aspect of the invention, a combination product as herein described and claimed is a kit-of-parts combination.

Yet another aspect of the invention is a pharmaceutical formulation or a capsule filled with said formulation as herein described and claimed, comprising a further therapeutic agent useful for the treatment of hypersomnia.

Yet an aspect of the invention is a combination product comprising,
 (i) a pharmaceutical formulation as herein described and claimed; and
 (ii) a therapeutic agent useful for the treatment of hypersomnia.

The further therapeutic agent useful for the treatment of hypersomnia may be selected from anyone of sodium oxybate (Xyrem®), modafinil (Provigil®), armodafinil (Nuvigil®), methylphenidate, amphetamine, (R)-2-amino-3-phenylpropylcarbamate hydrochloride (JZP-110), JZP-507, JZP-258, oxalate such as escitalopram oxalate, and pitolisant)(Wakix®).

In yet an aspect of the invention, the combination product as herein described is a kit-of-parts combination.

Yet an aspect of the invention is a drug product which is bioequivalent to a pharmaceutical formulation or bioequivalent to a combination, as herein described and claimed.

MEDICAL USES AND MEDICAL TREATMENT

Patients suffering from hepatic encephalopathy may show symptoms including, but not limited to, impairments of the sleep-wake cycle, cognition, memory, learning, motor coordination, consciousness, decreased energy levels and personality change, cognitive impairment, disorientation and coma.

An aspect of the present invention is a method for the treatment of hepatic encephalopathy, wherein a pharmaceutical formulation as herein described and claimed, is administered to a subject in need of such treatment.

Yet aspect of the invention is a method for the prevention of hepatic encephalopathy, wherein a pharmaceutical formulation as herein described and claimed, is administered to a subject in need of such treatment.

Yet an aspect of the invention is a pharmaceutical formulation as herein described and claimed, for use in a method for the treatment or prevention of hepatic encephalopathy.

Yet an aspect of the invention is the use of a a pharmaceutical formulation as herein described and claimed for the manufacture of a medicament for the treatment or prevention of hepatic encephalopathy.

In one embodiment of the invention, said hepatic encephalopathy is selected from any one of type A hepatic encephalopathy, type B hepatic encephalopathy, type C hepatic encephalopathy, minimal hepatic encephalopathy, and overt hepatic encephalopathy.

An aspect of the present invention is a method for the treatment of hypersomnolence, wherein a pharmaceutical formulation as herein described and claimed, is administered to a subject in need of such treatment.

Yet aspect of the invention is a method for the prevention of hypersomnolence, wherein a pharmaceutical formulation as herein described and claimed, is administered to a subject in need of such treatment.

Yet an aspect of the invention is a pharmaceutical formulation as herein described and claimed, for use in a method for the treatment or prevention of hypersomnolence.

Yet an aspect of the invention is the use of a a pharmaceutical formulation as herein described and claimed, for the manufacture of a medicament for the treatment or prevention of hypersomnolence.

In one embodiment of the invention, the hypersomnolence is selected from the group consisting of idiopathic hypersomnia, recurrent hypersomnia, narcolepsy, shift work sleeping disorder, excessive sleepiness, endozepine-related recurrent stupor, and amphetamine-resistant hypersomnia.

In certain further embodiments, the hypersomnolence is related to a disorder selected from the group consisting of restless leg syndrome, nocturnal dystonia, nocturnal movement disorder, Klein-Levin syndrome, Parkinson's disease, a disorder related to a medication or substance, a psychiatric disorder, rapid eye movement (REM) behaviour disorder, frontal nocturnal dystonia, nocturnal movement disorder, obstructive sleep apnoea, liver cirrhosis and hepatic encephalopathy.

ADMINISTRATION ROUTES

The pharmaceutical formulation as herein described and claimed, may be administered by enteral administration. Examples of enteral administration involves administration to the esophagus, stomach, and small and large intestines (i.e., the gastrointestinal tract). Methods of administration include oral, sublingual (dissolving the drug under the tongue), and rectal.

In one aspect of the invention, the pharmaceutical formulation according to the present invention is administered orally.

PROCESS FOR THE PREPARATION OF FORMULATIONS

A pharmaceutical formulation according to the present invention is manufactured by preheating the vehicle as herein defined to a suitable temperature, whereafter 3α-ethynyl-3β-hydroxyandrostan-17-one oxime, optionally in micronized form, is added to said vehicle under stirring at a suitable temperature and until a clear solution has been obtained.

3α-Ethynyl-3β-hydroxyandrostan-17-one oxime may be prepared by following the synthetic procedure as described in the published patent application WO 2008/063128.

One aspect of the invention is a process for making a pharmaceutical formulation as herein described and claimed, whereby:
 (i) the vehicle as herein described and claimed is heated to a temperature of from 15° C.-80° C.; and
 (ii) 3α-ethynyl-3β-hydroxyandrostan-17-one oxime, optionally in micronized form, is added to the vehicle under stirring and at a temperature of from 15° C.-80° C. until the compound has been completely dissolved and a clear solution is provided, whereafter the solution is optionally filled into a capsule.

In one aspect of the invention the temperature for heating the vehicle in step (i) above is from 60° C.-75° C.

In one aspect of the invention the temperature is decreased to approximately 30° C. for capsule filling.

Yet an aspect of the invention, is a pharmaceutical formulation obtainable by any one process as herein described and claimed.

EXAMPLES

The solubility of 3α-ethynyl-3β-hydroxyandrostan-17-one oxime (Compound I) was tested in different vehicles.

General Description

The solubility of Compound I was evaluated in different vehicles. Compound I was weighed into small vials and a known amount of a vehicle was added. The sample was heated, if required to melt the vehicle, to approx. from 15° C.-80° C. and agitated by vortex or stirrer. More Compound I or vehicle was added to evaluate the solubility of Compound I in the system by visual inspection.

Example 1

Capric/caprylic monoglyceride (1.02 g) [Imwitor® 742 obtained from IOI Oleo] was heated to 40° C. Micronized Compound I was added in aliquots and the mixture was agitated by vortex. Addition was continued until a clear solution was not longer obtained after mixing. A total of 28 mg of Compound I resulted in a clear solution but 31 mg did not dissolve.

Example 2

Glycerol monooleate [Cithrol GMO from Croda Health Care] was melted at 50° C. Micronized Compound I was weighed into a vial (3.9 mg) and glycerol monooloeate was added (413 mg). The sample was heated and agitated by vortex. A clear solution was not obtained. Additional glycerol monooleate (83 mg) resulted in a clear solution. The mixture appears to solidify at room temperature.

Example 3

Micronized Compound 1 (1.3 mg) was added to oleoyl macrogol-6 glyceride [Labrafil M1944 CS from Gattefossé] (0.91 g). The sample was heated to approx. 40° C. and agitated by vortex. A clear solution was obtained. Compound I was added (3.3 mg), still resulting in a clear solution after heating to 40° C. and agitation by vortex. Further addition of Compound I (3.0 mg) resulted in undissolved material after repeated agitation by vortex and heating.

Example 4

Micronized Compound I was weighed into a vial (1.8 mg) and propylenglycol monolaurate [Lauroglycol FCC from Gattefossé] was added (100 μL). The sample was agitated by vortex at room temperature. No clear solution was obtained. More proplenglycol monolaurate was added in portions (2×100 μL) and a clear solution was obtained after agitation by vortex.

Example 5

Micronized Compound I was weighed into a vial (25.9 mg) and propylenglycol monocaprylate Type I [Capryol PGMC from Gattefossé] was added (0.991 g). The sample was stirred in room temperature during approx. 60 minutes and resulted in undissolved material. Additional proplenglycol monocaprylate Type I (0.994 g) was added and a clear solution was obtained after 60 minutes of stirring at room temperature. Compound I (6 mg) was added and a clear solution was obtained again during stirring. Addition of Compound I (3 mg) resulted in undissolved material after stirring in room temperature during 60 minutes.

Example 6

Micronized Compound I was weighed into a vial (26.2 mg) and propylenglycol monocaprylate Type II [Capryol 90 from Gattefossé] was added (0.988 g). The sample was stirred in room temperature during approx. 60 minutes and resulted in undissolved material. Additional proplenglycol monocaprylate Type II (0.383 g) was added and a clear solution was obtained after 30 minutes of stirring at room temperature. Compound I (4.5 mg) was added and a clear solution was obtained again during stirring. Addition of Compound I (4.9 mg) resulted in undissolved material after stirring in room temperature during 60 minutes. Further addition of proplenglycol monocaprylate Type II (0.139 g) resulted in a clear solution after 60 minutes of agitation.

Example 7

Micronized Compound I was weighed into a vial (32.5 mg) and polyoxyethylene-8 caprylic/capric glyceride [Acconon MC8-2 from Abitec] was added (1.008 g). Stirring at room temperature for 30-60 minutes resulted in undissolved material. Polyoxyethylene-8 caprylic/capric glyceride was added in eight portions up to a total of 14.06 gram. The material was stirred at least 30 minutes between each addition. After the last addition a clear solution was obtained.

TABLE 1

Solubility of Compound I in different vehicles (Examples 1-7)

| Example | Carrier | Trademark | Solubility |
|---|---|---|---|
| 1 | Capric/caprylic glycerides | Imwitor ® 742 | 20-30 mg/g |
| 2 | Glyceryl monooleate | Cithrol GMO | 8 mg/g |
| 3 | Oleoyl macrogol-6 glycerides | Labrafil M1944 CS ® | 5 mg/g |
| 4 | Propylenglycol monolaurate type I | Lauroglycol FCC | 6 mg/g |
| 5 | Propylenglycol monocaprylate type I | Capryol PGMC | 15 mg/g |

TABLE 1-continued

Solubility of Compound I in different vehicles (Examples 1-7)

| Example | Carrier | Trademark | Solubility |
|---|---|---|---|
| 6 | Propylenglycol monocaprylate type II | Capryol 90 | 23 mg/g |
| 7 | Polyoxyethylene-8 caprylic/capric glycerides | Acconon MC8-2 | 2 mg/g |

Example 8A

Lipid Solution in Capsule

Capric/caprylic glyceride [Imwitor® 742] was heated to 60° C. and Compound I was added to a concentration of 20 mg/mL. Upon completed dissolution the temperature was decreased to 30° C. and the solution was filled in hard gelatin capsules of size 0. The target fill weight was 500 mg where after the capsules were capped.

Example 8B

Lipid Solution in Capsule

Capric/caprylic glyceride [Imwitor® 742] was heated to 60° C. and Compound I was added to a concentration of 2 mg/mL. Upon completed dissolution the temperature was decreased to 30° C. and the solution was filled in hard gelatin capsules of size 0. The target fill weight was 500 mg where after the capsules were capped.

Example 9

Lipid Solid in Capsule

Capric/caprylic glyceride [Imwitor® 742] was heated to 70° C. and Compound I was added to a concentration of 40 mg/mL. Upon completed dissolution the temperature was decreased to 30° C. and the solution was filled in hard gelatin capsules of size 0. The target fill weight was 500 mg where after the capsules were capped and kept at −20° C. for 2-3 hours before storage in refrigerator.

By increasing the heating temperature from 60° C. to 70° C., 40 mg/mL of Compound I could be dissolved instead of 20 mg/mL.

Example 10

The following pharmaceutical formulations were produced and used in the clinical Phase I study described below.

By following the manufacturing method as described in Example 8 A and 8 B, the following doses were filled into a hard gelatin capsule (size 0) for the clinical dosing. For the 10 mg capsules, 0.5 ml of the concentration 20 mg/ml as produced by Example 8 A were filled into each capsule. For the 1 mg capsules, 0.5 ml of the concentration 2 mg/ml as produced by Example 8B were filled into each capsule.

The placebo capsules contain the vehicle only, which was filled into the same type of capsules as for the capsules comprising compound I. The target fill weight was 500 mg.

| | Amount | Amount Capric/caprylic glyceride (Imwitor ® 742) | Clinical capsule dose |
|---|---|---|---|
| Compound I | 1 mg | 499 mg | 1 mg capsule |
| Compound I | 10 mg | 490 mg | 10 mg capsule |
| Placebo | — | 500 mg | — |

The 1 mg capsules were used for the 1 mg as well as for the 3 mg dosing in the clinical study. The 10 mg capsules were used for the higher dosing in the clinical study.

BIOLOGICAL STUDIES

I. Oral Absorption of 3α-ethynyl-3β-hydroxyandrostan-17-one oxime

In a study performed by the applicant of the present invention, the oral absorption of 3α-ethynyl-3β-hydroxyandrostan-17-one oxime was simulated in different animal species and man at different dose. The solubility in different media is shown in the following table:

| Media | Solubility |
|---|---|
| Water | 1.5 µg/ml |
| SGF (Simulated Gastric Fluid) | 0.2 µg/ml |
| FaSSIF (Fasted-State Simulated Intestinal Fluid) | 7.0 µg/ml |
| FeSSIF (Fed-State Simulated Intestinal Fluid) | 19.0 µg/ml |

The GI absorption (ACAT™) model within GastroPlus™ v9.0 was used to simulate the fraction and amount absorbed of 3α-ethynyl-3β-hydroxyandrostan-17-one oxime after oral administration. Absorption was simulated in rat, dog and human. Base line input parameters are summarized in Table A. The input parameters were chosen from the conditions used in earlier preclinical experiments or from those planned for in future studies. The particle size of 3α-ethynyl-3β-hydroxyandrostan-17-one oxime in clinical material is approx. 10 µm.

TABLE A

Dosing parameters used for simulations

| | Solution in capsule | Powder in capsule |
|---|---|---|
| Dose | 10, 100, 200 mg | 10, 100 and 200 mg |
| Dose volume | 1 ml | — |
| Precipitation time | 15 hours* | 0.25 hours |
| Particle radius | — | 10 µm |

*Artificial number to reflect that solubility in the vehicle does not change during passage through the small intestine.

The PK parameters used for simulations were taken from the PK result summary of the human clinical phase I single ascending dose (SAD) study described under item II below. The data used were from dose levels 10, 100 and 200 mg. The median value of clearance, volume of distribution, AUC, T1/2 (terminal), Cmax and Tmax were used. For volume of distribution a mean body weight of 70 kg was used to transform the volume of distribution from L to L/Kg. For plasma concentration-time data, the mean values were used.

The simulated (predicted) plasma concentration-time profiles following oral administration at different dose and formulation are summarized in Table B below together with the actual plasma concentration-time profiles observed in the clinical phase I study (cf. Table 1 below):

TABLE B

Predicted and observed PK parameters for 3α-ethynyl-3β-hydroxyandrostan-17-one oxime following oral administration in human.

| PK parameter | Dose (mg) | Fraction absorbed pred. (%) | $AUC_{0-24}$ obs. (µg·h/mL) | $AUC_{0-24}$ pred. (µg·h/mL) | Cmax obs. (µg/mL) | Cmax pred. (µg/mL) | Tmax obs. (hours) | Tmax pred. (hours) |
|---|---|---|---|---|---|---|---|---|
| Solution in capsule | 10 | 100 | 0.73 | 0.7 | 0.13 | 0.07 | 1 | 2 |
| Powder in capsule | 10 | 78 | | 0.6 | | 0.03 | | 13 |
| Solution in capsule | 100 | 100 | 10.8 | 8.8 | 1.5 | 0.6 | 1.5 | 2 |
| Powder in capsule | 100 | 24 | | 1.5 | | 0.08 | | 20 |
| Solution in capsule | 200 | 99 | 26.1 | 18.1 | 2.7 | 1.4 | 2 | 2 |
| Powder in capsule | 200 | 14 | | 1.8 | | 0.1 | | 20 |

Following oral administration of 3α-ethynyl-3β-hydroxyandrostan-17-one oxime solution in man, the predicted fraction absorbed is complete in the dose interval 10-200 mg. The predicted fraction absorbed is much less following administration of a powder in a capsule. Fractions absorbed of 78% and 14% were simulated for doses of 10 and 200 mg respectively. For the solution formulation, predicted Cmax values were approximately 2-fold lower than the Cmax values that were actually observed in man following administration of a lipid in capsule. The AUC and the Tmax were between 70 and 100% of the observed values. The PK input parameters that were used for simulations do not take into account effects of for example protein binding, blood/plasma ratio, and multi-compartment kinetics and may therefore explain the discrepancies between observed and simulated plasma concentration time profiles. Another factor could be the permeability input parameter that was used. A higher in-vivo permeability in man than the experimental in-vitro permeability value that was used in simulations may result in higher peak plasma concentrations.

Nevertheless, the simulation with an oral aqueous solution could predict the plasma concentration profiles that were obtained for capsules containing medium chain monoglycerides rather well. For simulations with the oral aqueous solutions, it was assumed that the entire dose of 3α-ethynyl-3β-hydroxyandrostan-17-one oxime was in solution without any precipitation occurring during passage through the small intestine. This indicates that 3α-ethynyl-3β-hydroxyandrostan-17-one oxime in medium chain monoglycerides behaves like an aqueous solution without precipitation with respect to oral absorption.

Simulated absorption from a powder capsule was much less than absorption from the solution capsules. AUC and Cmax were decreased 10 and 20-fold at 100 and 200 mg oral doses. Simulated oral absorption from a powder in capsule shows a predicted maximum plasma concentration of approximately 100 ng/ml for oral doses of more than 100 mg.

Solubility rather than dissolution is the limiting parameter for oral absorption at high dose (>100 mg). Micronization of 3α-ethynyl-3β-hydroxyandrostan-17-one oxime in the powder in capsule that will result in improved dissolution due to increased particle surface area will therefore have limited effect on the total amount absorbed and the maximum plasma concentration.

Improved solubility on the other hand is predicted to have significant effect on oral absorption and maximum plasma concentrations obtained after powder in capsule formulations. Improved solubility in the GI tract may be observed in combination with intake of food. For powder in capsules it is therefore predicted that fasted or fed conditions will result in significant effects on 3α-ethynyl-3β-hydroxyandrostan-17-one oxime plasma concentrations and contribute to variability in absorption. Such effects are not expected for the lipid formulation from the current simulations. In vivo data will be needed to verify this as many other food effects may influence oral absorption that were not accounted for in the current study.

II. Clinical Phase I Study

The oral absorption of 3α-ethynyl-3β-hydroxyandrostan-17-one oxime, was studied in a phase I clinical study in human volunteers. The oral formulation in the phase I study was a capsule containing a lipid solution of said compound. Oral absorption in humans was found to give good plasma exposure with a Tmax between 1 and 2 hours and a dose linearity in the Cmax in the dose range of 1-200 mg. Also, it was shown that 3α-ethynyl-3β-hydroxyandrostan-17-one oxime when administered orally, enters the human brain and antagonizes the effects of the neurosteroid allopregnanolone at the GABA-A receptor at doses which are well tolerated and associated with linear pharmacokinetics.

Study Design

In total 90 eligible healthy consenting male subjects (age 18-50 years) were included in the study. The oral formulation used was a capsule containing a lipid solution of 3α-ethynyl-3β-hydroxyandrostan-17-one oxime formulated according to Example 10 above (IND formulation in the following).

The first in human single ascending dose (SAD) study (EudraCT 2015-004911-19) and the 5 day multiple ascending dose (MAD) study (EudraCT 2016-003651-30) were prospective, randomized, double-blinded and placebo-controlled and designed to assess the safety, tolerability and pharmacokinetic (PK) characteristics of single and multiple ascending oral doses of 3α-ethynyl-3β-hydroxyandrostan-17-one oxime (IND compound) in healthy male volunteers.

The IND formulation was orally administered in the following doses:
SAD: 1, 3, 10, 30, 100 and 200 mg.
MAD: 50 mg once daily; 50 mg twice daily (BID), i.e. 100 mg/day; or 100 mg twice daily (BID), i.e. 200 mg/day.

The antagonist study, with the purpose of evaluating the biological activity of the IND compound, (EudraCT 2015-004911-19) was randomized and placebo-controlled with a double-blind three-part cross-over design. Study subjects orally received: placebo (A); 3 mg of IND formulation (B); or 30 mg of IND formulation (C); followed 90 minutes later by an intravenous (i.v.) allopregnanolone injection (0.05 mg/kg) and repeated measurements of maximal saccadic eye velocity (SEV) (*Saccadometer Plus*, Ober Consulting Sp. z o.o, Poland) and sedation/somnolence (visual analogue scale graded from "Absence of sleepiness" to "Falling asleep) for three hours.

Analyses of the IND Compound and Allopregnanolone

The IND compound and allopregnanolone were quantified by UPLC/MS/MS Waters Acquity, C18 column, and Waters XEVO-TQ-S triple quadrupole mass spectrometer. As internal standards D4-[3α-ethynyl-3β-hydroxyandrostan-17-one oxime] and D5-allopregnanolone were used, respectively. For analysis of allopregnanolone oxime-derivatization was used to increase sensitivity. Standard- and QC-samples were prepared into human blank plasma/serum. The detection limit for 3α-ethynyl-3β-hydroxyandrostan-17-one oxime was 1 ng/mL, and for allopregnanolone 0.05 ng/ml (0.15 nmol/L).

Data Analyses

Pharmacokinetic parameters were evaluated using Non-Compartmental Analysis and the software Phoenix WinNonlin® version 6.3 or later (Pharsight Corporation, U.S.A.). Dose proportionality was for the SAD study based on $AUC_{0->\infty}$ and $C_{max}$, and in the MAD study on steady-state $AUC_\tau$. The accumulation ratio between the first and last dose was calculated as (steady-state $AUC_\tau$/first dose $AUC_{0->\infty}$). Statistical calculations were with IBM SPSS statistics (Version 24, IBM).

Results

Pharmacokinetics

Figure 2A:
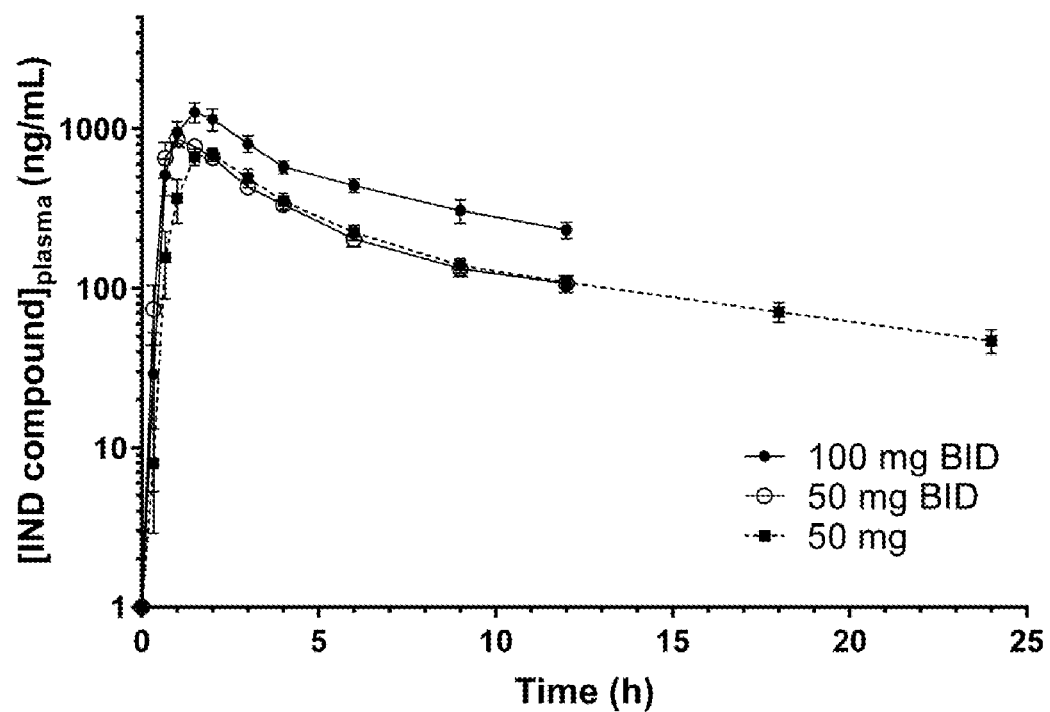
FIG. 2A shows the plasma concentration of the IND compound 3α-ethynyl-3β-hydroxyandrostan-17-one oxime (mean±SEM) after the first single oral dose in the MAD study (MAD study first dose). Dosing in the MAD study was with 50 mg once daily, 50 mg twice daily (i.e. 100 mg) and 100 mg twice daily (i.e. 200 mg), six subjects per dose.
Figure 2B:
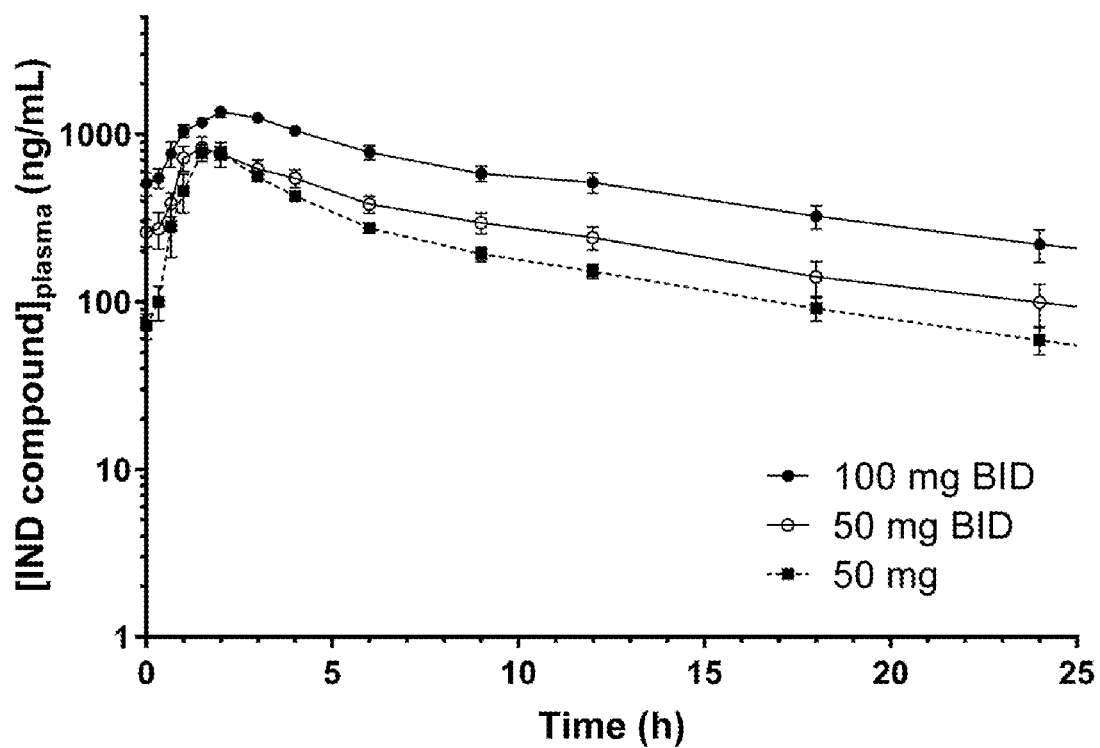
FIG. 2B shows the plasma concentration of the IND compound 3α-ethynyl-3β-hydroxyandrostan-17-one oxime (mean±SEM) after repeated dosing for five days (last dose of the MAD study). Dosing was with 50 mg once daily, 50 mg twice daily (i.e. 100 mg) and 100 mg twice daily (i.e. 200 mg), six subjects per dose.

After single dosing with the IND formulation, the plasma concentration increased proportionally to the increase in dose with proportionality constants 13 of 1.01 for CMax and of 1.12 for $AUC_{0>\infty}$ (Table 1, FIG. 1). Also dosing for 5 days twice daily, resulted in proportional increase in plasma concentration of the IND compound 3α-ethynyl-3β-hydroxyandrostan-17-one oxime with dose, with 1.9 times increase in $AUC_{0->\infty}$ when the dose was doubled from 50 to 100 mg, and with very little accumulation, 1.1-1.2 times (Table 1, FIG. 2).

IND Compound Antagonism of Allopregnanolone-Induced Decreased SEV 30 mg of the IND compound significantly inhibited the allopregnanolone-induced decrease in SEV (analysis of AUC, p=0.04, Table 2) during the responsive time period of subjects that responded to the allopregnanolone injection with a decrease in SEV (n=11, 69%). While the diminution of the allopregnanolone effect by 3 mg of IND compound was non-significant (p=0.286).

IND Compound Antagonism of Allopregnanolone-Induced Sedation

For subjects that responded to the allopregnanolone injection with sedation (n=8, 50%) the statistical analysis showed that both 3 and 30 mg of the IND compound significantly inhibited the sedative effect during the responsive time period (p=0.012 and p=0.05, respectively, Table 2).

Exposures to allopregnanolone

At the three study occasions the serum allopregnanolone concentration curves were very similar with the highest serum level at the first study time point after the i.v. injection, 74-82 nM. There were no significant differences between the allopregnanolone exposures during the three study occasions, (p=0.163, comparisons of AUC).

Discussion

The present findings demonstrate that orally administered 3α-ethynyl-3β-hydroxyandrostan-17-one oxime when formulated in a fatty acid ester according to the present invention, is well tolerated in humans. Adverse events (AEs) were generally mild and neither serious adverse events (SAEs) nor dose-limiting toxicity was observed up to the highest doses administered to healthy adults males in the single (200 mg) or multiple (100 mg every 12 hours for 5 days) ascending dose protocols. At all doses studied, 3α-ethynyl-3β-hydroxyandrostan-17-one oxime exhibited linear PK; i.e., both $C_{max}$ (SAD) and systemic exposure assessed as $AUC_{0->\infty}$ (SAD) or $AUC_\tau$ (steady-state) were linearly related to oral dose and there was no evidence of drug accumulation during steady state dosing.

Importantly, the results of the challenge study shows that 3α-ethynyl-3β-hydroxyandrostan-17-one oxime enters the brain and antagonizes the effects of allopregnanolone at the GABA-A receptor. Orally administered 3α-ethynyl-3β-hydroxyandrostan-17-one oxime produced apparent dose-dependent inhibition of the effects of allopregnanolone. SEV was significantly inhibited by 30 mg 3α-ethynyl-3β-hydroxyandrostan-17-one oxime with an intermediate, but non-significant, inhibition at 3 mg.

3α-ethynyl-3β-hydroxyandrostan-17-one oxime also significantly reversed allopregnanolone-induced sedation at both the 3 and 30 mg doses, again in apparent dose dependent fashion.

The favorable safety and pharmacokinetic findings as well as the results of the allopregnanolone challenge study suggest that 3α-ethynyl-3β-hydroxyandrostan-17-one oxime formulated in accordance with the present invention represents a promising new treatment for human disorders attributable to the CNS effects of neurosteroids. Hepatic encephalopathy (HE), a neurological disorder associated with cirrhosis and portal-systemic shunting in which elevated brain levels of allopregnanolone have been reported (Ahboucha et al. 2005 and 2006) is one example.

The findings of the antagonist study extend the earlier findings in animal models suggesting that 3α-ethynyl-3β-hydroxyandrostan-17-one oxime antagonizes the effects of allopregnanolone at concentrations likely to be pathophysiologically relevant. The serum allopregnanolone concentrations in the antagonist study 10 min after injection averaged about 80 nM, considerably higher than concentrations of 6-20 nmol/kg in the brain of cirrhotic patients who died in hepatic coma (Ahboucha et al. 2005 & 2006). Moreover, animal studies indicate that the concentration vs. time profile for 3α-ethynyl-3β-hydroxyandrostan-17-one oxime (unpublished data) and allopregnanolone (Johansson et al. 2002) are very similar in brain and plasma. The results imply that 3α-ethynyl-3β-hydroxyandrostan-17-one oxime administered at doses as low as 30 mg, well within the range that is well tolerated in adult males, can reverse the effects of neurosteroids even at concentrations higher than those described in HE patients.

Several recent observations also implicate neurosteroid-induced allosteric activation of CNS GABA-A receptors in the excessive daytime sleepiness (EDS) associated with disorders such as idiopathic hypersomnia (Billiard and Sonka, 2016). These include the identification of a putative GABA-A agonist in the CSF of patients with primary hypersomnia (Rye 2012) and the clinical observation that the GABA-A antagonist flumazenil can promote wakefulness in patients with EDS (Korkmaz 1997). Indeed, the clinical manifestations of HE and hypersomnolence disorders exhibit similarities, and HE has been considered a sleepiness disorder (Montagnese 2015).

In summary, these findings show that 3α-ethynyl-3β-hydroxyandrostan-17-one oxime administered orally to humans as a pharmaceutical formulation as herein described and claimed, antagonizes the effects of the neurosteroid allopregnanolone at the GABA-A receptor in the brain at doses which are well tolerated and associated with linear pharmacokinetics. This suggests that 3α-ethynyl-3β-hydroxyandrostan-17-one oxime may also be able to normalize GABAergic neurotransmission and represents a promising new therapeutic for treatment of disorders associated with hypersomnolence or other disorders attributable to neurosteroid-mediated allosteric over-activation of GABA-A receptors.

TABLE 2

Statistical analysis of allopregnanolone-responding subjects during the responsive period. Change in maximal saccadic eye velocity (ΔSEV) shown as area under the curve (AUC), and change in sedation shown as AUC of VAS scores. Statistical analysis with Wilcoxon's signed rank test showed significant antagonism by Compound I towards allopregnanolone-induced changes in SEV and sedation.

|  | Allopregnanolone + placebo | Allopregnanolone + Compound I 3 mg | Allopregnanolone + Compound I 30 mg |
| --- | --- | --- | --- |
| AUC (ΔSEV) (deg/s × min) | −3018 ± 656 | −1592 ± 924 N.S. | −909 ± 798 p = 0.04* |
| AUC (ΔSedation) (mm × min) | 1928 ± 404 | 698 ± 332 p = 0.01* | 416 ± 469 p = 0.05* |

*Significantly different to Allopregnanolone + placebo,
N.S = non significant

The invention claimed is:
1. A pharmaceutical formulation comprising:
   (i) 3α-ethynyl-3β-hydroxyandrostan-17-one oxime

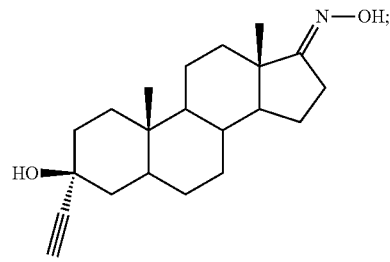

and
   (ii) a vehicle comprising
      (a) 45-100% of a monoester of propylene glycol;
      (b) optionally up to 51% of a diester of propylene glycol;

TABLE 1

Plasma concentrations of 3α-ethynyl-3β-hydroxyandrostan-17-one oxime (Compound I) and pharmacokinetic parameters presented as mean (SD), six subjects per dose.

| Treatment with Compound I | Dose increase* | $C_{Max}$ (ng/mL) | $C_{Max}$ increase* | $AUC_{0-\infty}$ (ng · h/mL) | $AUC_\tau$ (ng · h/mL) | AUC increase* |
| --- | --- | --- | --- | --- | --- | --- |
| Single dose: | | | | | | |
| 1 mg | — | 13 (3.2) | — | 67 (13) | | — |
| 3 mg | 3 | 44 (8.6) | 3.4 | 215 (16) | | 3.2 |
| 10 mg | 3.33 | 149 (18) | 3.4 | 785 (178) | | 3.7 |
| 30 mg | 3 | 464 (58) | 3.1 | 2565 (291) | | 3.3 |
| 100 mg | 3.33 | 1525 (669) | 3.3 | 11861 (3357) | | 4.6 |
| 200 mg | 2 | 2775 (491) | 1.8 | 25827 (7080) | | 2.2 |
| Multiple dose: (day 1): | | | | | | |
| 50 mg | — | 772 (131) | — | 4894 (1098) | | — |
| 50 mg BID (i.e. 100 mg) | — | 911 (183) | — | 4293 (989) | | — |
| 100 mg BID (i.e. 200 mg) | 2 | 1314 (388) | 1.4 | 8201 (1357) | | 1.9 |
| Multiple dose: (steady-state, day 5): | | | | | | |
| 50 mg | — | 892 (188) | — | | 5174 (857)[a] | — |
| 50 mg BID (i.e. 100 mg) | — | 924 (256) | — | | 5202 (1585)[b] | — |
| 100 mg BID (i.e. 200 mg) | 2 | 1440 (204) | 1.6 | | 9898 (1607)[b] | 1.9 |

* fold increase versus next lower dose,
[a] τ = 24 hours,
[b] τ =12 hours wherein the monoester and/or diester (if any) comprises a fatty acid selected from one or more of caprylic acid (C8) in an amount of 50-90%;
  capric acid (C10) in an amount of 10-50%;
  caproic acid (C6) in an amount of up to 3%;
  lauric acid (C12) in an amount of up to 100%;
  palmitic acid (C16) in an amount of up to 12%;
  myristic acid (C14) in an amount of up to 3%;
  stearic acid (C18) in an amount of up to 6%;
  oleic acid (C18:1) in an amount of up to 100%;
  linoleic acid (C18:2) in an amount of up to 35%; and
wherein
the amount of 3α-ethynyl-3β-hydroxyandrostan-17-one oxime is from 0.1-10% by weight of the total weight of the composition.

2. The pharmaceutical formulation according to claim 1, wherein the formulation consists of 3α-ethynyl-3β-hydroxyandrostan-17-one oxime and the vehicle only.

3. The pharmaceutical formulation according to claim 1, wherein the vehicle is a monoester of propylene glycol.

4. The pharmaceutical formulation according to claim 3, wherein said monoester of propylene glycol is selected from any one of propylene glycol caprylate, propylene glycol caproate, and propylene glycol decanoate.

5. The pharmaceutical formulation according to claim 3, wherein said monoester of propylene glycol is selected from any one of propylene glycol palmitate, propylene glycol stearate, and propylene glycol linoleate.

6. The pharmaceutical formulation according to claim 1, wherein the vehicle comprises a monoester and a diester of propylene glycol.

7. The pharmaceutical formulation according to claim 6, wherein said diester of propylene glycol is selected from propylene glycol dicaproate, propylene glycol dicaprylate, propylene glycol didecanoate, propylene glycol dilaurate, propylene glycol dimyristate, propylene glycol dipalmitate, propylene glycol distearate, propylene glycol dioleate, and propylene glycol dilinoleate.

8. The pharmaceutical formulation according to claim 1, wherein the vehicle is propylene glycol monolaurate.

9. The pharmaceutical formulation according to claim 1, wherein the vehicle is propylene glycol monocaprylate.

10. The pharmaceutical formulation according to claim 1, wherein the amount of 3α-ethynyl-3β-hydroxyandrostan-17-one oxime is from 0.1-5% by weight of the total weight of the formulation, or from 0.1-4% by weight of the total weight of the formulation.

11. The pharmaceutical formulation according to claim 10, wherein the amount of vehicle in said pharmaceutical formulation is from 90-99.9% by weight of the total weight of the formulation.

12. The pharmaceutical formulation according to claim 10, wherein the amount of vehicle in said pharmaceutical formulation is 95-99.9% by weight of the total weight of the formulation.

13. The pharmaceutical formulation according to claim 1, wherein the formulation is filled into a capsule.

14. The pharmaceutical formulation according to claim 13, wherein the capsule comprises from 5 mg-40 mg of 3α-ethynyl-3β-hydroxyandrostan-17-one oxime.

15. The pharmaceutical formulation according to claim 14, wherein the capsule comprises from 10 mg-20 mg of 3α-ethynyl-3β-hydroxyandrostan-17-one oxime.

16. The pharmaceutical formulation according to claim 15, comprising a further therapeutic agent used as standard of care therapy for hepatic encephalopathy.

17. The pharmaceutical formulation according to claim 16, wherein the further therapeutic agent is an ammonia-lowering compound.

18. The pharmaceutical formulation according to claim 17, wherein the ammonia-lowering compound is selected from rifaximin, lactulose, ornithine phenylacetate, and glycerol phenylbutyrate.

19. A method for the treatment of hepatic encephalopathy, whereby the pharmaceutical formulation according to claim 1, is administered to a patient in need of such treatment.

20. The method according to claim 19, wherein a dose of from 1 mg to 200 mg of 3α-ethynyl-3β-hydroxyandrostan-17-one oxime is administered to said patient.

21. The method according to claim 19, wherein a dose of from 30 mg to 60 mg of 3α-ethynyl-3β-hydroxyandrostan-17-one oxime is administered to said patient.

22. The method according to claim 19, wherein a daily dosage of from 1 mg/day to 200 mg/day of 3α-ethynyl-3β-hydroxyandrostan-17-one oxime is administered to said patient.

* * * * *